(12) United States Patent
Ludwig et al.

(10) Patent No.: US 8,411,923 B2
(45) Date of Patent: Apr. 2, 2013

(54) TOMOGRAPHIC IMAGE RECONSTRUCTION METHOD AND APPARATUS USING FILTERED BACK PROJECTION

(75) Inventors: Jasmina Ludwig, München (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 964 days.

(21) Appl. No.: 12/483,416

(22) Filed: Jun. 12, 2009

(65) Prior Publication Data

US 2009/0310844 A1    Dec. 17, 2009

(30) Foreign Application Priority Data

Jun. 13, 2008    (DE) .................. 10 2008 028 387

(51) Int. Cl.
*G06K 9/00*    (2006.01)

(52) U.S. Cl. ........ 382/131; 382/128; 382/132; 382/260; 382/276; 382/294; 378/4; 378/62

(58) Field of Classification Search ........................ None
See application file for complete search history.

(56) References Cited

U.S. PATENT DOCUMENTS

| | | | | |
|---|---|---|---|---|
| 5,153,516 A * | 10/1992 | Gopalsami et al. | ............ | 324/309 |
| 6,256,370 B1 * | 7/2001 | Yavuz | .............................. | 378/22 |
| 6,442,288 B1 * | 8/2002 | Haerer et al. | ................. | 382/128 |
| 6,707,878 B2 * | 3/2004 | Claus et al. | ..................... | 378/22 |
| 7,447,295 B2 | 11/2008 | Hoheisel et al. | | |
| 2005/0058240 A1 | 3/2005 | Claus | | |
| 2006/0102846 A1 * | 5/2006 | Manjeshwar et al. | ... | 250/363.03 |
| 2007/0093711 A1 * | 4/2007 | Hoheisel et al. | ............. | 600/407 |
| 2007/0217569 A1 * | 9/2007 | Barth et al. | ..................... | 378/22 |
| 2007/0280404 A1 * | 12/2007 | Nielsen et al. | .................... | 378/4 |
| 2008/0107324 A1 | 5/2008 | Hseih et al. | | |
| 2009/0190814 A1 * | 7/2009 | Bouman et al. | ............... | 382/131 |

OTHER PUBLICATIONS

Betzler et al., ("MATLAB") ["Fitting in MATLAB", 2003, University of Osnabrück].*
"Einführung in die Computertomographie, Mathematischphysikalische Grundlagen der Bildrekonstruktion," Buzug (2003), pp. 198-199.
"Optimizing Filtered Backprojection Reconstruction for a Breast tomosynthesis Prototype Device," Mertelmeier et al., Advanced Optical and Quantum Memories and Computing III, Proc. of the SPIE, vol. 6142 (2006), pp. 131-142.

* cited by examiner

*Primary Examiner* — Matthew Bella
*Assistant Examiner* — Jason Heidemann
(74) *Attorney, Agent, or Firm* — Schiff Hardin LLP

(57) ABSTRACT

In a tomographical image reconstruction method and apparatus to generate an image of an examination subject from a number of digital projection data acquired at different projection angles, a first analytical filter kernel (formed by a first analytical function) is determined for a filtered back projection in the spatial frequency range, this first analytical filter kernel approximating, at least in a range of the spatial frequency, a discrete filter kernel iteratively determined for a model. Back projection is implemented with a second analytical filter kernel calculated from the analytical filter kernel and formed by a second analytical function.

10 Claims, 4 Drawing Sheets

US 8,411,923 B2

TOMOGRAPHIC IMAGE RECONSTRUCTION METHOD AND APPARATUS USING FILTERED BACK PROJECTION

BACKGROUND OF THE INVENTION

1. Field of the Invention

The present invention concerns a tomographical image reconstruction method for generation of an image of an examination subject. The present invention also concerns an imaging device operating according to such a method.

2. Description of the Prior Art

Tomographical image reconstruction is a computerized method that allows a two-dimensional image or a three-dimensional volume image of the examination subject to be generated from projection (two-dimensional) data acquired at different projection angles.

For this purpose, a number of mathematical algorithms are known, among which include iterative, algebraic reconstruction methods that have proven to be particularly suitable for conventional computed tomography (CT) operating with x-ray radiation as well as for tomosynthesis (likewise operating with x-ray radiation).

Tomosynthesis is an imaging method in which individual images or projection data of an examination subject are acquired in a number of different projection directions with a digital x-ray detector. Through image reconstruction methods, a three-dimensional image data set can be generated from these individual digital images (i.e. from the image data belonging to these individual images) acquired from different projection angles in a limited angle range (for example between −25° and +25° relative to the normal of the acquisition surface of the x-ray detector). The three-dimensional image data set is composed of a number of slice images that respectively render a slice of the breast oriented parallel to the acquisition surface of the x-ray detector, for example. Tomosynthesis is used to generate three-dimensional x-ray images of the breast, for example.

The tomosynthetic slice images generated with an iterative algebraic reconstruction method exhibit a very high similarity to conventional mammography images with regard to the ability to differentiate between dense and less dense tissue, such that their interpretation by radiologists familiar with such mammography images is made easier.

The long computation times incurred with iterative algebraic reconstruction methods, however, are disadvantageous. For this reason, filtered back projection is normally used as a reconstruction method, both in conventional CT and in tomosynthesis.

In filtered back projection, the metadata provided by the x-ray detector are filtered and projected back to a volume matrix—the digital, three-dimensional image of a partial volume of the subject. It is one of the most promising reconstruction methods since it is based on an analytical algorithm that can be derived from the scan geometry and is numerically very efficient and stable.

A significant problem in filtered back projection is the provision of suitable filters with which it is possible for the physical measurement method that is used and the geometry that is used (for example conventional CT or tomosynthesis with limited angle range) to generate tomographic images with high clarity in order to differentiate benign from malignant variations and in order to be able to reduce the number of incorrect findings, i.e. the number of the suspected findings that are caused by non-malignant variations and the number of undetected malignant tumors.

A particularly promising approach to this is known from DE 10 2005 050 917 A1, in which a discrete filter kernel suitable for filtered back projection is calculated with an iterative algebraic reconstruction method. These discrete filter kernels can then be inserted into the filtered back projection instead of typical filter kernels. The desired image quality therefore results in a short calculation time. The discrete filter kernels calculated with this method are generated with a test subject (for example a wireframe model) and optimized with regard to this test subject, but not with regard to a real examination subject and the concrete, diagnostic question. Such an optimization would require the use of a number of such discrete filter kernels calculated via iterative, algebraic reconstruction, with correspondingly high measurement and calculation cost.

SUMMARY OF THE INVENTION

An object of the present invention is to provide a tomographical image reconstruction method to generate an image of an examination subject in which the advantages of filtered back projection are combined with the advantages of the iterative algebraic image reconstruction. A further object of the invention is to provide an imaging device operation according to this method.

In the tomographical image reconstruction method according to the invention, an image of an examination subject is generated by filtered back projection from a number of digital projection data acquired from different projection angles. Initially, a first analytical filter kernel formed by a first analytical function is determined that, at least in one range of the spatial frequency, approximates an iteratively determined filter kernel for a test subject. The back projection is subsequently implemented with a second analytical filter kernel calculated from the first analytical filter kernel and formed by a second analytical function.

A high flexibility in the determination of a filter kernel optimized for the imaging or diagnostic task to be performed is possible through the determination of an analytical filter kernel that can be represented by a first analytical function. This analytical filter kernel is determined from a discrete filter kernel iteratively determined with an algebraic reconstruction method (meaning the approximation of the discrete filter kernel via a continuous function from which a second analytical filter kernel can be calculated by mathematical operations).

The calculation of the second analytical filter kernel advantageously ensues so that its curve has a shape similar to the first analytical filter kernel, and in particular the curve initially rises in the tomosynthetic image reconstruction with increasing spatial frequency, exhibits a maximum as well as a subsequent turning point, takes a value of zero upon approaching an upper limit frequency, and advantageously has a positive value at a frequency of zero. The advantageous properties of the iterative filter kernel are thereby largely retained.

Particularly in tomosynthetic image reconstruction, an approximation of the first and/or second analytical function by a 4th-degree polynomial has proven to be suitable.

The above object also is achieved in accordance with the present invention by a device constructed and operating in order to implement the method described above, as well as all embodiments described above.

DESCRIPTION OF THE PREFERRED EMBODIMENTS

Figure 1:
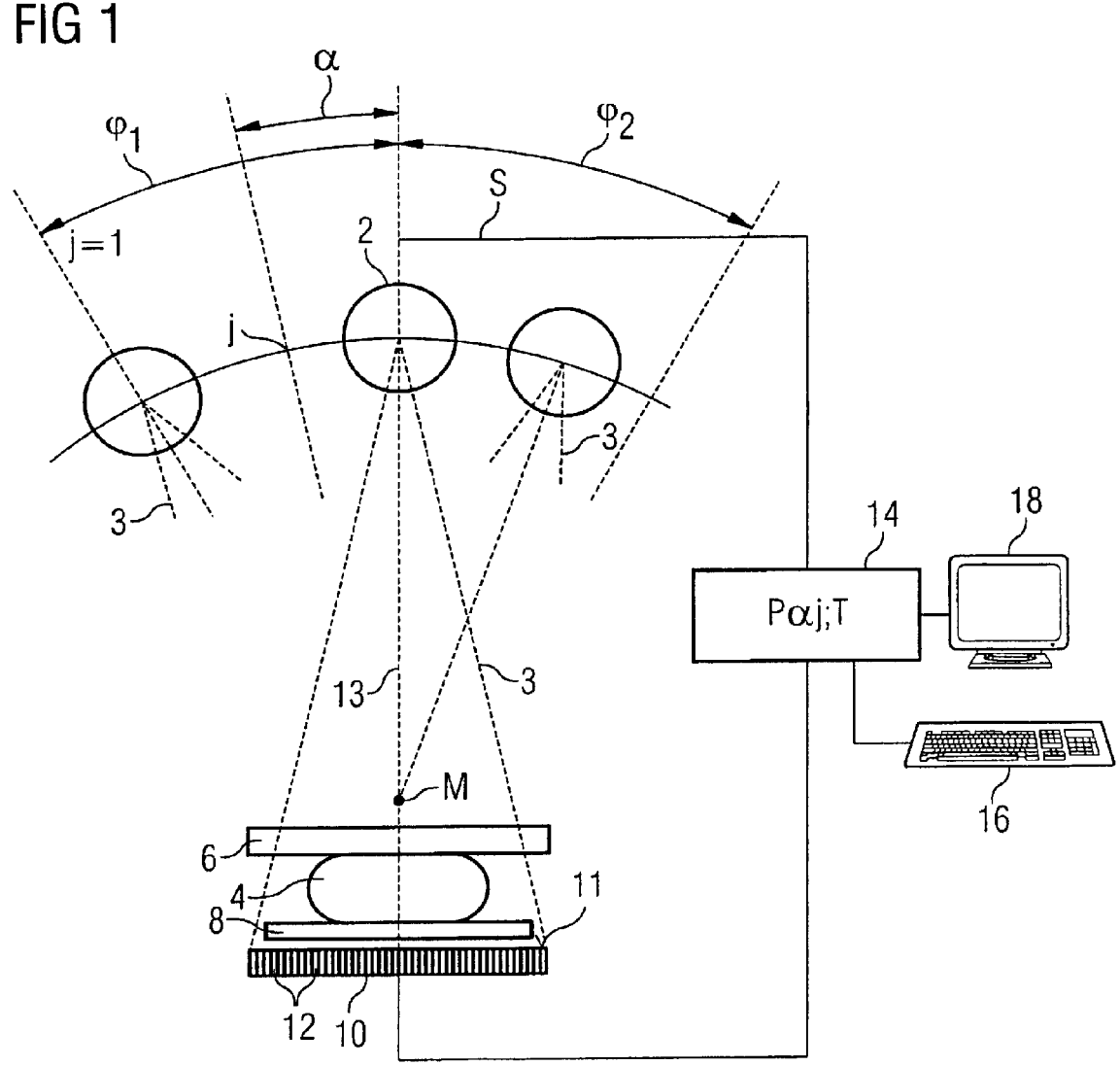
FIG. 1 schematically illustrates an embodiment of an imaging device according to the invention in a schematic, principle representation.

As shown in FIG. 1, the imaging device (in the exemplary embodiment a mammography apparatus provided for the generation of tomosynthetic images) has an x-ray tube 2 for the generation of x-rays 3 that penetrate an examination subject 4. The examination subject 4 is a female breast that is held between a compression plate 6 and a support plate 8. The x-rays 3 penetrating the examination subject 4, the compression plate 6 and the support plate 8 are received by a large-surface digital x-ray detector 10 that is constructed of a number of individual detectors 12 arranged in a matrix-like array, and whose acquisition surface 11 is arranged parallel to the plates 6, 8.

The x-ray tube 2 is mounted such that its location can be adjusted in a limited range relative to the examination subject, and can for example be pivoted into different angle positions j=1 ... n in a limited angle range $\phi_1$, $\phi_2$ on an axis M perpendicular to the plane of the drawing. Individual images of the examination subject 4 thus can be generated with different projection angles $\alpha_j$ relative to the normal 13 of the acquisition surface 11 of the x-ray detector 10. The angle range $\phi_1$, $\phi_2$ does not have to be symmetrical to the normal 13. These individual images, or the projection data $P_{\alpha j}$ respectively associated therewith, are combined via reconstruction into a tomosynthetic 3D x-ray image T in a control and evaluation device 14 in an image computer, and the tomosynthetic 3D x-ray image T is presented on a monitor 18. In the illustrated embodiment, the x-ray detector 10 is stationary during the pivot movement of the x-ray tube 2, but in principle it is also possible to pivot the x-ray detector 10 as well, or to displace it linearly following the pivot movement of the x-ray tube 2.

Movement of the x-ray tube 2 on a limited, linear path instead of pivoting, so that the height difference between x-ray detector 10 and x-ray tube remains constant, is also possible. This linear path likewise does not necessarily have to proceed symmetrically to the normal 13. Given such a linear movement, an alignment of the x-ray tube 2 on the examination subject 4 ensues, such that in this case as well individual images of the examination subject 4 are also acquired from different projection angles $\alpha_j$ but in a limited angle range.

The control of the angle position j or—in the case of a linear displacement—of the linear position and of the alignment of the x-ray tube 2 as well as its operating parameters, ensues by control signals S that are generated by the control and evaluation device 14. Various analytical filter kernels (explained in the following) that are used for the filtered back projection can be selected by the user with the aid of input elements (symbolically illustrated in the example by a keyboard 16), and an image reconstruction ensuing with these filter kernels can be implemented.

For the imaging device depicted in the example of FIG. 1, a discrete filter kernel for the filtered back projection is now iteratively determined for every projection angle for a test subject (for example a wireframe model) with a method known from DE 10 2005 050 917 A1. Such a discrete filter kernel $k(x_i)$ iteratively determined for the filtering in the frequency range is plotted in FIG. 2 for the projection angle $\alpha=0°$ against the normalized spatial frequency $x=v/v_g$ (provided by the ratio of spatial frequency v and Nyquist frequency $v_g$) for discrete, normalized spatial frequency $x_i$ and is represented by points. This discrete filter kernel $k(x_i)$ can now be approximated by a first, analytical function (meaning that it can be represented by a first analytical function) with first filter kernel p(x) that is expressed by the solid curve. In the exemplary embodiment, the approximation of the discrete, iterative filter kernel $k(x_i)$ is a 4th-degree polynomial $$p(x)=p_4x^4+p_3x^3+p_2x^2+p_1x+p_0 \text{ with } p(x_i)\approx k(x_i)$$

Figure 2:
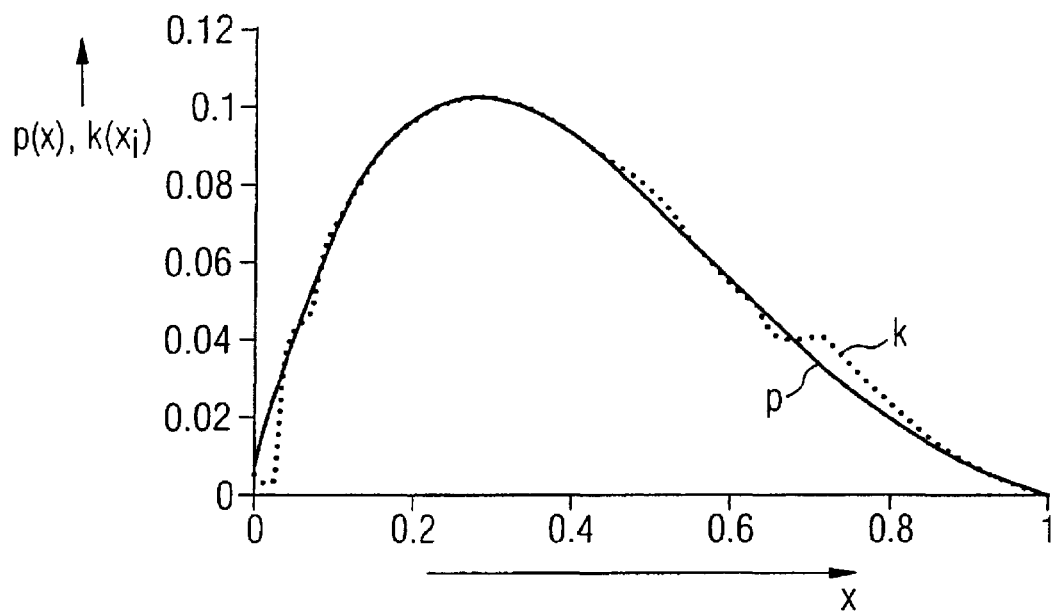
FIG. 2 is a diagram in which a discrete filter kernel calculated with an iterative, algebraic reconstruction method and a first analytical filter kernel approximated to this discrete filter kernel are plotted against the normalized spatial frequency.

Instead of the discrete filter kernel $k(x_i)$ stored in a look-up table, the first analytical filter kernel p(x) represented by the curve p rendered in FIG. 2 can now be used for the filtered back projection. Such a discrete filter kernel $k(x_i)$ and an associated first analytical filter kernel p(x) is now generated for each projection data set $P_{\alpha j}$. The use of such first analytical filter kernels p(x) now enables a simple optimization of the filter kernel in order to modify the image properties of the tomosynthetic slice images generated with filtered back projection, adapted to the diagnostic question on which an examination is based, in that a broad agreement is achieved with the image impression imparted by the images generated in conventional mammography, for example.

For this a second analytical filter kernel q(x) that can be represented by a second analytical function is determined from the first analytical filter kernel p(x), which second analytical filter kernel q(x) proceeds from the first analytical filter kernel p(x) by parameterization of a second analytical function Q(x) (which can be represented by a 4th-degree polynomial) with freely selectable D, N and C via the following rules:

$$Q(x)=Q_4x^4+Q_3x^3+Q_2x^2+Q_1x+Q_0$$

$$Q_0=Dp_0$$

$$Q_4+Q_3+Q_2+Q_1+Q_0=0$$

$$Q(x_1)=Cp(x_1)$$

$$Q(x_3)=Cp(x_3)$$

$Q'(x_2)=0$ for $x_2$, given that $p'(x_2)=0$
(Q' and p' are first derivatives according to x)
And q(x)=Q(x/N) with q(x)=0 for $x \geq N$ The sample points $x_1$, $x_2$ and $x_3$ are advantageously located in the following intervals:

$$0.25 \leq x_1 \leq 0.35;\ 0.2 \leq x_2 \leq 0.3;\ 0.8 \leq x_3 \leq 1.$$

In the exemplary embodiments shown in FIGS. 2 through 6, the following sample points were used:

$$x_1=0.3,\ x_2=0.28 \text{ and } x_3=0.99$$

The contrast of the reconstructed image can be altered with the aid of the parameter C. The reconstruction result can be interpreted as a combination of unfiltered and filtered back projection with $Q_0 \neq 0$, wherein the parameter D defines the proportion of unfiltered projection. The parameter D therefore affects the ability to differentiate tissue types of different density, for example adipose tissue and glandular tissue. The parameter N defines the cut-off spatial frequency and corresponds to an upper limit frequency. It affects the image noise and enables the adaptation of the filter kernel to the spatial resolution, i.e. the spacing of the respective, possibly binned (the image data of multiple detector elements are combined) detector elements of the x-ray detector that are used.

Figure 3:
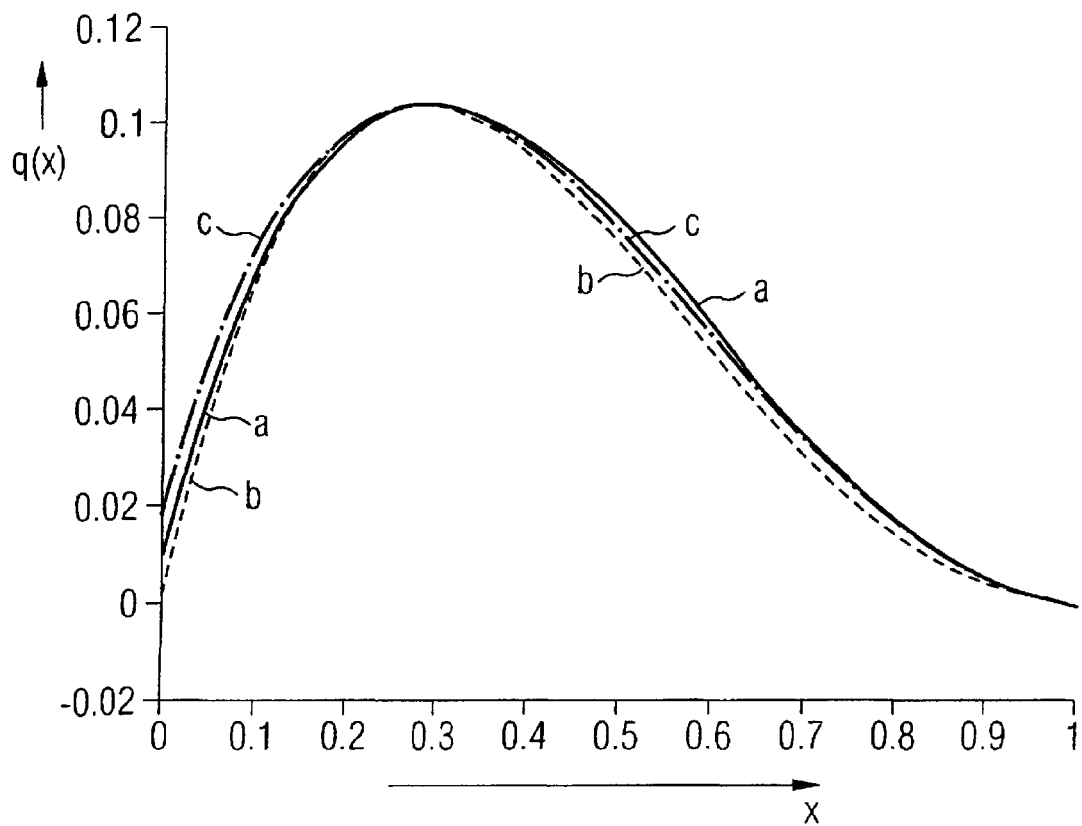
FIGS. 3 through 7 respectively show diagrams in which different second analytical filter kernels derived from the first analytical filter kernel are plotted against the normalized spatial frequency.

FIG. 3 shows the influence of the parameter D on the curve shape of the second analytical filter kernel q(x). The solid curve a corresponds to the first analytical filter kernel p(x)(p(x)=Q(x)=q(x) when C=1, D=1 and N=1). The filter kernels represented by the dashed curve b and the dash-dot curve c are derived from this first analytical filter kernel p(x) by changing the parameter D. The curve b is associated with the parameter D=0.125. The parameter D=2 belongs to curve c.

Figure 4:
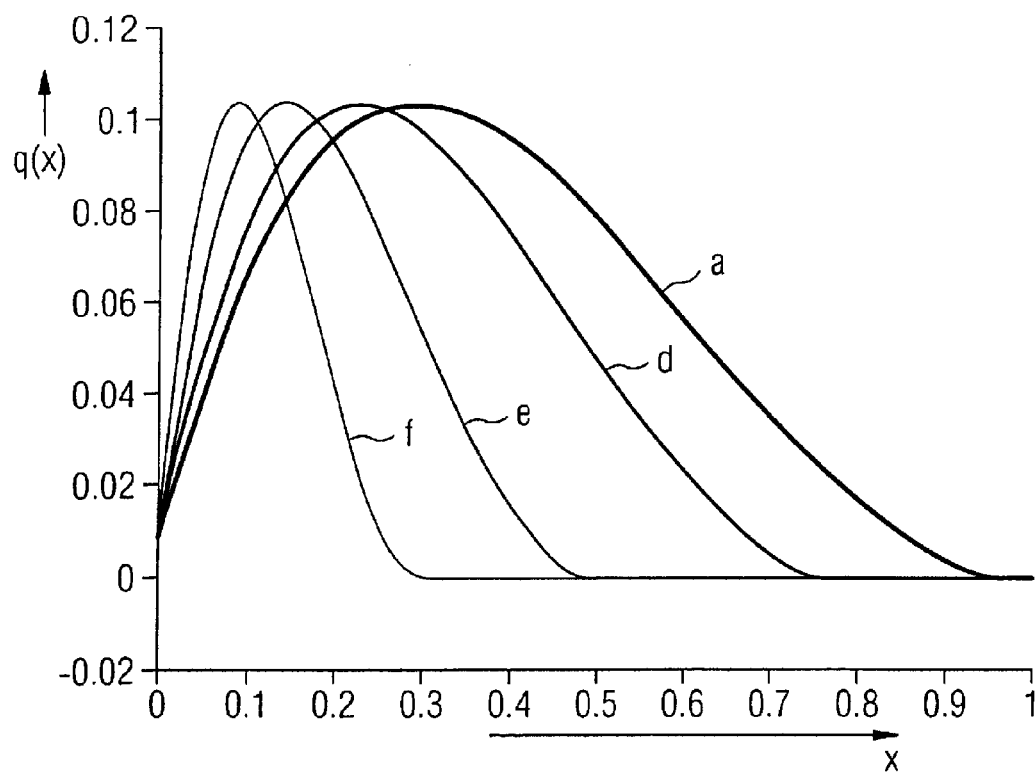

The change of the curve shape of the first analytical filter kernel p(x) that is produced solely via variation of the cut-off parameter N is illustrated in the diagram of FIG. 4. Curve d belongs to N=0.8, curve e to N=0.5 and curve f to N=0.3.

Figure 5:
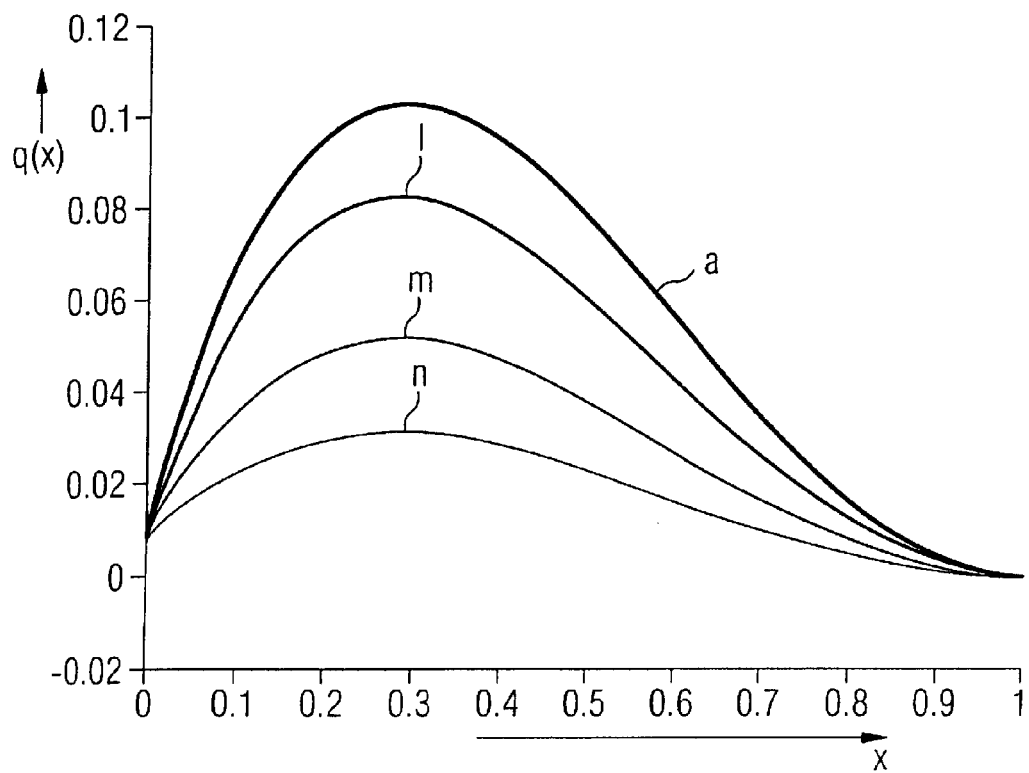

FIG. 5 shows the affect of parameter C. Curve l belongs to C=0.8, curve m to C=0.5 and curve n to C=0.3.

Figure 6:
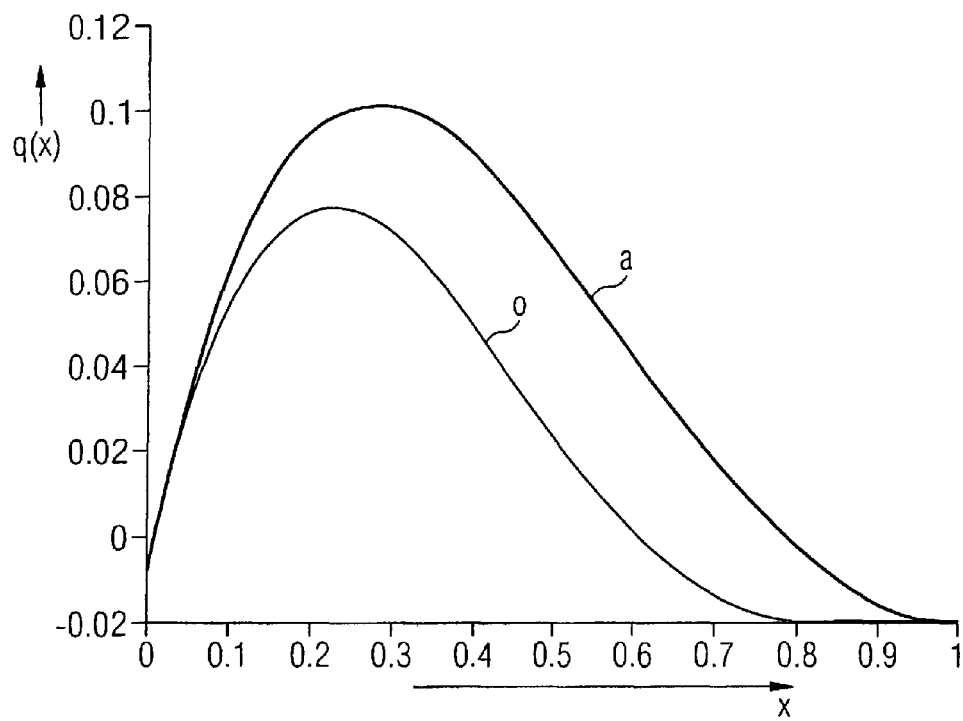

The curve o rendered in the diagram of FIG. 6 belongs to the parameter set D=1, C=N=0.8.

As an alternative to the procedure described in the preceding in the determination of the second analytical filter kernel q(x), this can be generated via the following rules:

$$Q_a(x) = p(x) + \lambda_a(1-x)^n$$

with $\lambda_a > -p_0$ and n a natural number with $n \leq 4$ $$Q_b(x) = Q_a(x) + \lambda_b(x/x_2)^n \text{ for } x \leq x_2,$$

$$Q_b(x) = Q_a(x) + \lambda_b((x-1)/(x_2-1))^n \text{ for } x > x_2$$

wherein $|\lambda_b| < 1$ and the first analytical filter kernel p(x) is maximal at $x_2$
and $$q(x) = Q_b(x/N) \text{ with } q(x) = 0 \text{ for } x \leq N.$$

Figure 7:
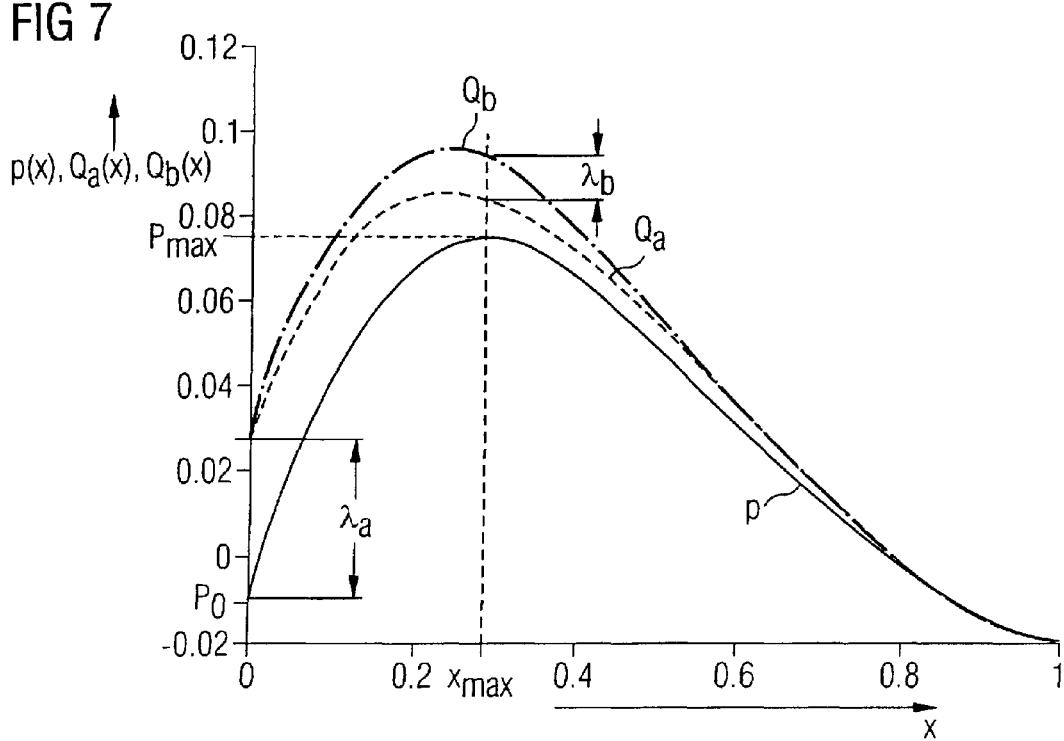

The effect of the parameters $\lambda_a$ and $\lambda_b$ is illustrated in FIG. 7. There the first analytical filter kernel p(x) as well As auxiliary functions $Q_a(x)$ and $Q_b(x)$ (calculated with the preceding formulae) are plotted in a diagram in a basic drawing for positive parameters $\lambda_a$ and $\lambda_b$ against the spatial frequency x. The auxiliary functions $Q_a(x)$ and $Q_b(x)$ are also 4th-degree polynomials due to the calculation rules with n<4 that are indicated above.

The calculation rules for the second analytical filter kernel are advantageously selected so that the second analytical filter kernel q(x) has a shape similar to the first filter kernel p(x), i.e. initially rises (as in the present example of the first filter kernel p(x)) with increasing spatial frequency, exhibits a maximum (maximum of the first filter kernel $p_{max} = p(x_{max})$) as well as a subsequent turning point, and approximately assumes a value of zero at x=N.

As an alternative to the procedure illustrated in the preceding, according to which for every projection angle $\alpha_j$ (FIG. 1) a first analytical filter kernel $p_j(x)$ associated only with said projection angle $\alpha_j$ is derived from the discrete filter kernel $k_j(x_i)$ determined at this projection angle $\alpha_j$, and from this a second analytical filter kernel $q_j(x)$ is calculated. In a simplified embodiment, all projections can also be filtered with the same second analytical filter kernel q(x). For this purpose, an average discrete filter kernel is determined from the respective iteratively determined discrete filter kernels $k_j(x_i)$ for each projection angle $\alpha_j$, this average discrete filter kernel then being approximated by a first analytical filter kernel p(x) from which in turn a second analytical filter kernel q(x) is calculated by parameterization. This second analytical filter kernel q(x) is used for all projection angles $\alpha_j$.

The second analytical filter kernels according to the invention can be combined with other filters. In particular a combination is possible with a type of filter known as the "Slice Thickness" filter described in T. Mertelmeier, J. Orman, W. Haerer, M. K. Kumar, "Optimizing filtered back projection reconstruction for a breast tomosynthesis prototype device", Proc. SPIE Proc. 6142, 61420F-1-12 (2006). With such a "Slice Thickness" filter, artifacts are reduced, and an adjustment of the thickness of the slice rendered in a slice image is possible.

The slice images reconstructed with a filter kernel according to the invention can additionally be post-processed with digital image processing methods in order to improve the presentation of the border region of the breast, for example (peripheral equalization).

Although modifications and changes may be suggested by those skilled in the art, it is the intention of the inventors to embody within the patent warranted hereon all changes and modifications as reasonably and properly come within the scope of their contribution to the art.

We claim as our invention:

1. A tomographical image reconstruction method for reconstructing an image of a subject from a plurality of sets of digital projection data respectively acquired from the subject at different projection angles in an angle range, said method comprising the steps of:

in a processor, forming a first analytical filter kernel using a first analytical function, for a filtered back projection in a spatial frequency domain, that approximates, at least in a frequency range of said spatial frequency domain, a discrete filter kernel iteratively determined for a model; and from said sets of digital projection data, reconstructing an image of the subject by filtered back projection operating on said sets of digital projection data with said first analytical filter kernel and with a second analytical filter kernel calculated from said first analytical filter kernel and formed by a second analytical function, to obtain a set of image data representing the reconstructed image of the subject.

2. An image reconstruction method as claimed in claim 1 comprising determining said second analytical filter kernel as a function that initially increases with increasing spatial frequency, exhibits a maximum and a subsequent turning point, and has a value of approximately zero at an upper limit frequency.

3. An image reconstruction method as claimed in claim 2 comprising calculating said second analytical filter kernel as a function having a positive value when said spatial frequency is zero.

4. An image reconstruction method as claimed in claim 2 comprising employing a fourth degree polynomial as said second analytical function.

5. An image reconstruction method as claimed in claim 4 comprising employing a fourth degree polynomial as said first analytical function.

6. An image reconstruction method as claimed in claim 1 comprising, for each projection angle, determining a second analytical filter kernel in said processor respectively derived from said first analytical filter kernel that approximates a discrete filter kernel iteratively determined in a model for that projection angle, at least in said spatial frequency range.

7. An image reconstruction method as claimed in claim 1 comprising employing the same analytical filter kernel for each of said projection angles.

8. An image reconstruction method as claimed in claim 7 comprising determining said second analytical filter kernel in said processor as an average discrete filter kernel formed by averaging respective discrete filter kernels iteratively determined for different ones of said projection angles.

9. An image reconstruction method as claimed in claim 1 comprising combining said second analytical filter kernel with a slice thickness filter for use in said filtered back projection.

10. A tomographical image reconstruction device for reconstructing an image of a subject from a plurality of sets of digital projection data respectively acquired from the subject at different projection angles in an angle range, said device comprising:

a processor configured to form a first analytical filter kernel using a first analytical function, for a filtered back projection in a spatial frequency domain, that approximates, at least in a frequency range of said spatial frequency domain, a discrete filter kernel iteratively determined for a model; and said processor being configured to reconstruct, from said sets of digital projection data, an image of the subject by filtered back projection operating on said sets of digital projection data with said first analytical filter kernel and with a second analytical filter kernel calculated from said first analytical filter kernel and formed by a second analytical function, to obtain a set of image data representing the reconstructed image of the subject.

* * * * *